(12) United States Patent
Ito et al.

(10) Patent No.: US 11,931,718 B2
(45) Date of Patent: Mar. 19, 2024

(54) WATER-ABSORBING RESIN PARTICLES (71) Applicant: SUMITOMO SEIKA CHEMICALS CO., LTD., Hyogo (JP)

(72) Inventors: Takashi Ito, Himeji (JP); Miki Sakoda, Himeji (JP); Mutsumi Matsuoka, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 813 days.

(21) Appl. No.: 17/040,465

(22) PCT Filed: Mar. 27, 2019

(86) PCT No.: PCT/JP2019/013397
§ 371 (c)(1),
(2) Date: Sep. 22, 2020

(87) PCT Pub. No.: WO2019/189485
PCT Pub. Date: Oct. 3, 2019

(65) Prior Publication Data
US 2021/0023530 A1    Jan. 28, 2021

(30) Foreign Application Priority Data

Mar. 28, 2018 (JP) ................................ 2018-062075

(51) Int. Cl.
*B01J 20/26* (2006.01)
*A61F 13/15* (2006.01)
*B01J 20/28* (2006.01)
*G01N 11/00* (2006.01)
*C08F 20/06* (2006.01)

(52) U.S. Cl.
CPC ....... *B01J 20/261* (2013.01); *A61F 13/15203* (2013.01); *B01J 20/28016* (2013.01); *G01N 11/00* (2013.01); *A61F 2013/15463* (2013.01); *C08F 20/06* (2013.01)

(58) Field of Classification Search
CPC .... B01J 20/26; B01J 20/261; B01J 20/28016; A61F 13/15203; A61F 2013/15463; G01N 11/00; C08F 20/06
USPC ........................................................ 502/402
See application file for complete search history.

(56) References Cited

FOREIGN PATENT DOCUMENTS

| CN | 1056111 | 11/1991 |
|---|---|---|
| CN | 1056248 | 11/1991 |
| CN | 1461317 | 12/2003 |
| CN | 106715543 | 5/2017 |
| CN | 110446727 | 11/2019 |
| EP | 0629411 | 12/1994 |
| EP | 0697217 | 2/1996 |
| JP | S62-223203 | 10/1987 |
| JP | S62-254841 | 11/1987 |
| JP | S62-254842 | 11/1987 |
| JP | H5-239122 | 9/1993 |
| JP | H5-506164 | 9/1993 |
| JP | H5-506263 | 9/1993 |
| JP | H7-088171 | 4/1995 |
| JP | H9-503954 | 4/1997 |
| JP | 2002-514934 | 5/2002 |
| JP | 2003-088552 | 3/2003 |
| JP | 2006-143972 | 6/2006 |
| JP | 2014-108165 | 6/2014 |
| JP | 2017-179658 | 10/2017 |
| KR | 10-2014-0056225 | 5/2014 |
| KR | 10-2018-0022883 | 3/2018 |
| WO | 91/015177 | 10/1991 |
| WO | 91/015368 | 10/1991 |
| WO | 95/022358 | 8/1995 |
| WO | 96/004024 | 2/1996 |
| WO | 01/079314 | 10/2001 |
| WO | 02/085959 | 10/2002 |
| WO | 2016/052537 | 4/2016 |
| WO | 2016/158975 | 10/2016 |
| WO | 2018/181548 | 10/2018 |
| WO | 2019/189445 | 10/2019 |

OTHER PUBLICATIONS

The extended European search report issued for European Patent Application No. 19776383.2, dated Apr. 22, 2022, 5 pages.
International Search Report of PCT/JP2019/013397, dated Jul. 2, 2019, 2 pages.
Fredric L. Buchholz, Andrew T. Graham, "Modern Superabsorbent Polymer Technology", WILEY-VCH, 1997, 34 pages.
International Preliminary Report on Patentability of PCT/JP2019/013397, dated Oct. 8, 2020, 7 pages.
L. R. G. Treloar, "The Physics of Rubber Elasticity", 1975, pp. 59-65.
Fredric L. Buchholz, Andrew T. Graham, "Modern Superabsorbent Polymer Technology", 1998, pp. 55-60, 97-103, and 167-172.
"Experimental Report Reproduction of Example 19 of EP0744435 A1", Sep. 4, 2019, 4 pages.

(Continued)

*Primary Examiner* — Edward M Johnson
(74) *Attorney, Agent, or Firm* — Hamre, Schumann, Mueller & Larson, P.C.

(57) ABSTRACT

Water-absorbing resin particles have a repulsion rate of 5% or more according to the formula $(h_3-h_2)/h_1 \times 100 (\%)$ when a cylinder with an inner diameter of 25.4 mm, which has a mesh-like bottom onto which 0.2 g of the water-absorbing resin particles are sprinkled, is placed in a container having ion exchange water in an amount of 30 times a mass of the water-absorbing resin particles, where $h_1$ represents a free swelling height (mm) of the water-absorbing resin particles after 1 minute from initiation of water absorption, $h_2$ represents a height (mm) of the water-absorbing resin particles after a load of $1.3 \times 10^3$ Pa is applied to the water-absorbing resin particles for 1 minute after 1 minute from initiation of the water absorption, and $h_3$ represents a height (mm) of the water-absorbing resin particles after 1 minute from release of the load applied when measuring $h_2$.

4 Claims, 1 Drawing Sheet

(56) References Cited

OTHER PUBLICATIONS

"Experimental Report Reproduction of Example 7 of EP0450922 A2", Sep. 4, 2019, 4 pages.
"Extract from ISO4664-1", submitted for Japanese Patent Application No. 2020-509269 on Nov. 25, 2021 (notification mailed to Applicant on Dec. 14, 2021), 1 page.

WATER-ABSORBING RESIN PARTICLES

TECHNICAL FIELD

The present invention relates to water-absorbing resin particles.

BACKGROUND ART

An absorbent containing water-absorbing resin particles is used in sanitary goods such as paper diapers and sanitary napkins. A conventional absorbent is generally a mixture of water-absorbing resin particles and fibrous materials such as pulp. An elasticity or a flexibility of the conventional absorbent is highly dependent on the amount of pulp contained in the absorbent.

CITATION LIST

Patent Literature

[Patent Literature 1] JP 2017-1.79658 A

SUMMARY OF INVENTION

Technical Problem

In recent years, the trend is toward thinner sanitary goods, and the use of pulp-less absorbent is considered. However, in a case where the amount of pulp used in the absorbent is reduced, a hardness of a water-absorbing resin becomes conspicuous, and the feeling when in use becomes harder. Therefore, in order to soften the feeling of the sanitary goods when in use, that is, to enhance an elasticity and a flexibility, members such as non-woven fabrics used for top sheets, back sheets, and the like are improved (for example, Patent Literature 1). On the other hand, the conventional water-absorbing resin particles do not have a sufficient elasticity after water absorption and, when used in the absorbent, do not have a sufficient flexibility when in use.

An object of the present invention is to provide water-absorbing resin particles having an excellent elasticity after water absorption when used in an absorbent.

Solution to Problem

The present invention provides water-absorbing resin particles having a repulsion rate represented by Formula (1) of 5% or more.

$$(h_3-h_2)/h_1 \times 100(\%) \qquad (1)$$

In Formula (1), when a cylinder with an inner diameter of 25.4 mm, which has a mesh-like bottom onto which 0.2 g of the water-absorbing resin particles are sprinkled, is placed in a container having ion exchange water in an amount of 30 times a mass of the water-absorbing resin particles such that the water-absorbing resin particles absorb the ion exchange water $h_1$ represents a free swelling height (mm) of the water-absorbing resin particles after 1 minute from initiation of the water absorption, $h_2$ represents a height (mm) of the water-absorbing resin particles after a load of $1.3 \times 1.0^3$ Pa is applied to the water-absorbing resin particles for 1 minute after 1 minute from initiation of the water absorption, and $h_3$ represents a height (mm) of the water-absorbing resin particles after 1 minute from release of the load applied when measuring $h_2$.

Since the water-absorbing resin particles have a sufficiently high repulsion rate after water absorption, the water-absorbing resin particles can have a sufficient elasticity after water absorption when used in an absorbent.

It is preferable that the water-absorbing resin particles have an absorption rate of physiological saline by a vortex method of 10 seconds or less.

It is preferable that the water-absorbing resin particles have the retention capacity of 15 to 39 gig.

Advantageous Effects of Invention

According to the present invention, water-absorbing resin particles having an excellent elasticity after absorbing water when used in an absorbent is provided.

DESCRIPTION OF EMBODIMENTS

Figure 1:
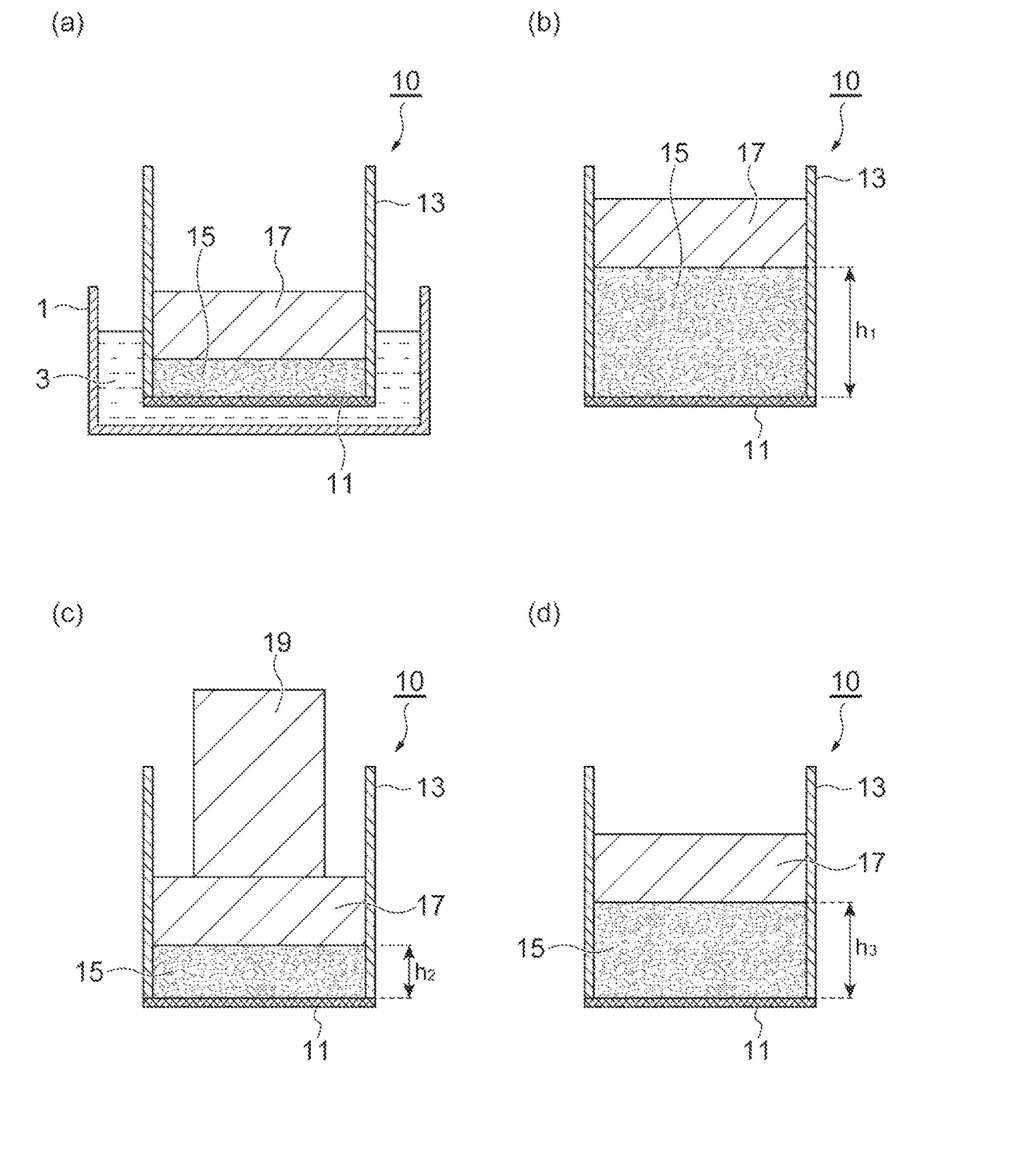
The FIGURE is a schematic view illustrating a method of measuring a repulsion rate of water-absorbing resin particles.

Hereinafter, suitable embodiments of the present invention will be described in detail. However, the present invention is not limited to the following embodiments. All configurations described in the present specification can be optionally combined without departing from the scope of the present invention. For example, numerical value ranges regarding various characteristics can be defined using the upper limit values and the lower limit values of the numerical ranges described in the present specification, or the numerical values optionally selected from the numerical values described in Examples as the upper limit values and the lower limit values.

Water-absorbing resin particles according to the present embodiment have a repulsion rate represented by Formula (1) of 5% or more.

$$(h_3-h_2)h_1(\%) \qquad (1)$$

In Formula (1), when a cylinder with an inner diameter of 25.4 mm, which has a mesh-like bottom onto which 0.2 g of the water-absorbing resin particles are sprinkled, is placed in a container having ion exchange water in an amount of 30 times a mass of the water-absorbing resin particles such that the water-absorbing resin particles absorb the ion exchange water, $h_1$ represents a free swelling height (mm) of the water-absorbing resin particles after 1 minute from initiation of the water absorption, $h_2$ represents a height (mm) of the water-absorbing resin particles after a load of $1.3 \times 10^3$ Pa is applied to the water-absorbing resin particles for 1 minute after 1 minute from initiation of the water absorption, and $h_3$ represents a height (mm) of the water-absorbing resin particles after 1 minute from release of the load applied when measuring $h_2$. An example of a detailed method of measuring the repulsion rate will be described in Examples below.

The repulsion rate of the water-absorbing resin particles according to the present embodiment is 5% or more, preferably 6% or more, more preferably 8% or more, and still more preferably 10% or more. It is preferable that the repulsion rate of the water-absorbing resin particles is the above-described value because an elasticity and a flexibility when used in an absorbent are enhanced. The repulsion rate of the water-absorbing resin particles according to the present embodiment may be 20% or less, 18% or less, 15% or less, or 12% or less.

In the water-absorbing resin particles according to the present embodiment, a ratio of the height under load $h_2$ to the free swelling height $h_1$ may be, for example, 0.94 or less, 0.92 or less, 0.90 or less, 0.88 or less, or 0.84 or less. The ratio of the height under load $h_2$ to the free swelling height $h_1$ may be, for example, 0.70 or more, 0.75 or more, or 0.78 or more.

In the water-absorbing resin particles according to the present embodiment, a ratio of the restored height $h_3$ to the height under load $h_2$ may be, for example, 1.06 or more, 1.08 or more, 1.10 or more, or 1.12 or more. The ratio of the restored height $h_3$ to the height under load $h_2$ may be, for example, 1.30 or less, 1.25 or less, or 1.22 or less.

As described above, the water-absorbing resin particles according to the present embodiment also have a high water absorption rate. In the water-absorbing resin particles according to the present embodiment, an absorption rate of physiological saline by a vortex method may be, for example, 10 seconds or less, preferably 7 seconds or less, and more preferably 5 seconds or less. A water absorption rate of the water-absorbing resin particles may be, for example, 1 second or more, and may be 2 seconds or more.

A retention capacity of physiological saline of the water-absorbing resin particles according to the present embodiment may be, for example, 15 to 39 g/g, or may be 15 to 36 g/g. The retention capacity of physiological saline and the absorption rate of physiological saline are measured by methods described in Examples which will be described later.

The water-absorbing resin particles according to the present embodiment can be produced, for example, by a production method described below. The water-absorbing resin particles according to the present embodiment may include, for example, a crosslinked polymer obtained by the polymerization of monomers containing water-soluble ethylenically unsaturated monomers.

Examples of a method for polymerizing the monomers include a reverse-phase suspension polymerization method, an aqueous solution polymerization method, a bulk polymerization method, and a precipitation polymerization method. Among these, from viewpoints of making it easy to secure favorable water absorption characteristics of the obtained water-absorbing resin particles and control of the polymerization reaction, the reverse-phase suspension polymerization method or the aqueous solution polymerization method is preferable.

In order to increase a specific surface area of the obtained water-absorbing resin particles, for example, a method in which a nonionic surfactant or an anionic surfactant with a hydrophilic-lipophilic balance (HLB) of 6 or more is used in the reverse-phase suspension polymerization method, a method in which a pyrolytic foaming agent such as an azo compound is used in the aqueous solution polymerization method, or the like can be adopted. Water-absorbing resin particles obtained by the method in which a nonionic surfactant or an anionic surfactant with an HLB of 6 or more is used in the reverse-phase suspension polymerization method among these methods can be suitably used. The HLB of the surfactant used in the reverse-phase suspension polymerization is more preferably 6 to 14, and still more preferably 8 to 12.

Hereinbelow, a method for polymerizing the water-soluble ethylenically unsaturated monomers will be described by way of an example of the reverse-phase suspension polymerization method.

Hereinafter, "acrylic" and "methacrylic" are collectively referred to as "(meth)acrylic". "Acrylate" and "methacrylate" are also referred to as "(meth)acrylate". Examples of the water-soluble ethylenically unsaturated monomer used in the production of the water-absorbing resin particles according to the present embodiment include (meth)acrylic acid and a salt thereof, 2-(meth)acrylamide-2-methylpropanesulfonic acid and a salt thereof, (meth)acrylamide, N,N-dimethyl (meth)acrylamide, 2-hydroxyethyl (meth)acrylate, N-methylol (meth)acrylamide, polyethylene glycol mono(meth)acrylate, N,N-diethylaminoethyl (meth)acrylate, N,N-diethylaminopropyl (meth)acrylate, and diethylaminopropyl (meth)acrylamide. In a case where the water-soluble ethylenically unsaturated monomer contains an amino group, the amino group may be quaternarized. A functional group such as a carboxyl group and an amino group, which is contained in the monomer, can function as a crosslinkable functional group in a post-crosslinking process which will be described later. These water-soluble ethylenically unsaturated monomers may be used alone or in a combination of two or more kinds thereof.

From a viewpoint of industrial availability, the water-soluble ethylenically unsaturated monomers preferably comprise, among these, at least one compound selected from the group consisting of acrylic acid and a salt thereof, methacrylic acid and a salt thereof, acrylamide, methacrylamide, and N,N-dimethyl acrylamide, and more preferably comprise at least one compound selected from the group consisting of acrylic acid and a salt thereof, methacrylic acid and a salt thereof, and acrylamide. The water-soluble ethylenically unsaturated monomers still more preferably comprise at least one compound selected from the group consisting of acrylic acid and a salt thereof, and methacrylic acid and a salt thereof, from a viewpoint of further enhancing the water absorption characteristics.

As the monomer, some of water-soluble monomers other than the above-described water-soluble ethylenically unsaturated monomers may also be used to an extent that exhibition of the effect of the present invention is not inhibited. Such a monomer can be used, for example, by mixing with an aqueous solution containing the water-soluble ethylenically unsaturated monomers. It is preferable that the amount of the water-soluble ethylenically unsaturated monomers to be used is 70% to 100% by mole with the total amount of the monomers. Above all, it is more preferable that acrylic acid and a salt thereof are in the amount of 70% to 100% by mole with the total amount of the monomers.

Usually, the water-soluble ethylenically unsaturated monomers are suitably used in a form of an aqueous solution. A concentration of the water-soluble ethylenically unsaturated monomers in an aqueous solution of the water-soluble ethylenically unsaturated monomers (hereinafter, referred to as an aqueous monomer solution) can usually be any value of 20% by mass or more and a saturated concentration or less, and is preferably 25% to 70% by mass, and more preferably 30% to 55% by mass. Examples of water to be used include tap water, distilled water, and ion exchange water.

In a case where the water-soluble ethylenically unsaturated monomer comprises an acid group, the aqueous monomer solution may be used after neutralizing the acid group with an alkaline neutralizing agent. From viewpoints of increasing the osmotic pressure of the obtained water-absorbing resin particles and further enhancing water absorption characteristics such as a water absorption rate, a degree of neutralization in the water-soluble ethylenically unsaturated monomers by the alkaline neutralizing agent is 10% to 100% by mole, preferably 50% to 90% by mole, and more preferably 60% to 80% by mole of the acidic groups in the water-soluble ethylenically unsaturated monomers. Examples of the alkaline neutralizing agent include alkali metal salts such as sodium hydroxide, sodium carbonate, sodium hydrogen carbonate, potassium hydroxide, and potassium carbonate; and ammonia. These alkaline neutralizing agents may be used in a form of an aqueous solution in order to simplify neutralizing operation. The above-mentioned alkaline neutralizing agents may be used alone or in combination of two or more kinds thereof. Neutralization of the acid groups of the water-soluble ethylenically unsaturated monomers can be performed by, for example, adding an aqueous solution of sodium hydroxide, potassium hydroxide, or the like dropwise to the aqueous monomer solution and mixing them.

In the reverse-phase suspension polymerization method, an aqueous monomer solution is dispersed in a hydrocarbon dispersion medium in the presence of a surfactant, and polymerization of the water-soluble ethylenically unsaturated monomers is performed using a water-soluble radical polymerization initiator or the like. An internal crosslinking agent may be used in the polymerization.

Examples of the surfactant include nonionic surfactants and anionic surfactants. Examples of the nonionic surfactants include sorbitan fatty acid esters, (poly)glycerin fatty acid esters ("(poly)" means both of a case with the prefix "poly" and a case without the prefix "poly", and the same applies hereinbelow.), sucrose fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkylphenyl ethers, polyoxyethylene castor oil, polyoxyethylene hydrogenated castor oil, alkylallyl formaldehyde condensed polyoxyethylene ethers, polyoxyethylene polyoxypropylene block copolymer, polyoxyethylene polyoxypropyl alkyl ethers, and polyethylene glycol fatty acid esters. Examples of the anionic surfactants include fatty acid salts, alkylbenzene sulfonate, alkylmethyl taurate, polyoxyethylene alkylphenyl ether sulfuric acid ester salts, polyoxyethylene alkyl ether sulfonic acid salts, phosphoric acid esters of polyoxyethylene alkyl ethers, and phosphoric acid esters of polyoxyethylene alkyl allyl ethers. Among these, from viewpoints of a favorable state of a W/O type reverse-phase suspension, facilitating the obtaining of water-absorbing resin particles with suitable particle diameters, and industrial availability, the surfactant preferably comprises at least one compound selected from the group consisting of sorbitan fatty acid esters, polyglycerin fatty acid esters, and sucrose fatty acid esters. Furthermore, from a viewpoint of improving the water absorption characteristics of the obtained water-absorbing resin particles, the surfactant more preferably comprises sorbitan fatty acid esters. These surfactants may be used alone or in combination of two or more kinds thereof.

From a viewpoint of obtaining sufficient effect on the amount of the surfactant to be used and from an economical viewpoint, the amount of the surfactant is preferably 0.1 to 5 parts by mass, more preferably 0.2 to 3 parts by mass, and still more preferably 0.5 to 2 parts by mass, with respect to 100 parts by mass of the aqueous solution of the water-soluble ethylenically unsaturated monomers.

Examples of the water-soluble radical polymerization initiator include persulfates such as potassium persulfate, ammonium persulfate, and sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxyisobutyrate, t-butyl peroxypivalate, and hydrogen peroxide; and azo compounds such as 2,2'-azobis(2-methylpropionamidine) dihydrochloride, 2,2'-azobis[2-(N-phenylamidino)propane] dihydrochloride, 2,2'-azobis[2-(N-allylamidino)propane] dihydrochloride, 2,2'-azobis {2-[1-(2-hydroxyethyl)-2-imidazolin-2-yl]propane} dihydrochloride, 2,2'-azobis {2-methyl-N-[1,1-bis(hydroxymethyl)-2-hydroxyethyl]propionamide}, 2,2'-azobis[2-methyl-N-(2-hydroxyethyl)-propionamide], and 4,4'-azobis(4-cyanovaleric acid). These radical polymerization initiators may be used alone or in combination of two or more kinds thereof. The term "water-soluble" of the water-soluble radical polymerization initiator in the present specification means that the radical polymerization initiator exhibits a solubility of 5% by mass or more in water at 25° C.

The amount of the water-soluble radical polymerization initiator to be used may be 0.005 to 1 mole with respect to 100 moles of the water-soluble ethylenically unsaturated monomers. In a case where the amount of the radical polymerization initiator to be used is 0.005 moles or more, the polymerization reaction does not require a long period of time, which is thus efficient. In a case where the amount of the radical polymerization initiator to be used is 1 mole or less, it is effective in preventing an abrupt polymerization reaction.

The water-soluble radical polymerization initiator can also be used as a redox polymerization initiator in combination with a reducing agent such as sodium sulfite, sodium hydrogen sulfite, ferrous sulfate, and L-ascorbic acid.

In order to control the water absorption characteristics of the water-absorbing resin particles in the polymerization reaction, a chain transfer agent may be contained in the aqueous solution of the water-soluble ethylenically unsaturated monomers used for polymerization. Examples of the chain transfer agent include hypophosphites, thiols, thiolic acids, secondary alcohols, and amines.

Examples of the hydrocarbon dispersion medium include chained aliphatic hydrocarbons such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons such as benzene, toluene, and xylene. These hydrocarbon dispersion media may be used alone or in combination of two or more kinds thereof. The hydrocarbon dispersion medium may comprise at least one compound selected from the group consisting of a chained aliphatic hydrocarbon having 6 to 8 carbon atoms and an alicyclic hydrocarbon having 6 to 8 carbon atoms. From viewpoints of a favorable state of a W/O type reverse-phase suspension, facilitating the obtaining of water-absorbing resin particles with high water absorption rates and suitable particle diameters, industrial availability, and stable quality, the hydrocarbon dispersion medium may comprise n-heptane, cyclohexane, or the both. In addition, from the same viewpoints, as a mixture of the hydrocarbon dispersion media, for example, Exxsol Heptane (manufactured by ExxonMobil Chemical: containing 75% to 85% of hydrocarbons of n-heptane and isomers thereof), which is commercially available, may be used.

From viewpoint of appropriately removing heat of polymerization and making it easy to control a polymerization temperature, the amount of the hydrocarbon dispersion medium to be used is preferably 100 to 1,000 parts by mass, more preferably 150 to 800 parts by mass, and still more preferably 200 to 700 parts by mass, with respect to 100 parts by mass of the water-soluble ethylenically unsaturated monomers. When the amount of the hydrocarbon dispersion medium to be used is 100 parts by mass or more, there is a tendency that it becomes easy to control the polymerization temperature. When the amount of the hydrocarbon dispersion medium to be used is 1,000 parts by mass or less, there is a tendency that the productivity of polymerization is improved, which is economical.

Internal crosslinking occurs by self-crosslinking upon the polymerization, but the water absorption characteristics of the water-absorbing resin particles may be controlled by carrying out internal crosslinking using further using an internal crosslinking agent. Examples of the internal crosslinking agent to be used include di- or tri(meth)acrylic acid esters of polyols such as ethylene glycol, propylene glycol, trimethylolpropane, glycerin, polyoxyethylene glycol, polyoxypropylene glycol, and polyglycerin; unsaturated polyesters obtained by reacting the polyols with unsaturated acids such as maleic acid and fumaric acid; bis(meth)acrylamides such as N,N'-methylenebis(meth)acrylamide; di- or tri(meth)acrylic acid esters obtained by reacting a polyepoxide with (meth)acrylic acid; carbamyl di(meth)acrylate esters obtained by reacting a polyisocyanate such as tolylene diisocyanate and hexamethylene diisocyanate with hydroxyethyl meth)acrylate, compounds having two or more polymerizable unsaturated groups, such as allylated starch, allylated cellulose, diallyl phthalate, N,N',N"-triallylisocyanate, and divinylbenzene; polyglycidyl compounds such as (poly)ethylene glycol diglycidyl ether, (poly)glycerin diglycidyl ether, (poly)glycerin triglycidyl ether, (poly)propylene glycol polyglycidyl ether, and polyglycerol polyglycidyl ether; haloepoxy compounds such as epichlorohydrin, epibromohydrin, and α-methyl epichlorohydrin; and compounds having two or more reactive functional groups, such as isocyanate compounds including, for example, 2,4-tolylene diisocyanate and hexamethylene diisocyanate. These crosslinking agents may be used alone or in combination of two or more kinds thereof.

From viewpoints of suppressing the properties of water solubility by appropriately crosslinking the obtained polymer and exhibiting sufficient water absorption amounts, the amount of the internal crosslinking agent is preferably 0 to 0.03 moles, more preferably 0 to 0.01 moles, and still more preferably 0 to 0.005 moles, per 1 mole of the water-soluble ethylenically unsaturated monomer.

The reverse-phase suspension polymerization is performed in a water-in-oil system by mixing water-soluble ethylenically unsaturated monomers, a water-soluble radical polymerization initiator, and as desired, an internal crosslinking agent, a surfactant, and a hydrocarbon dispersion medium with each other, and heating the mixture under stirring. The addition procedure of the respective components, and the like can be appropriately adjusted, but it is suitable that, for example, a surfactant and a hydrocarbon dispersion medium are mixed with each other in advance, a water-soluble radical polymerization initiator, an internal crosslinking agent, and water-soluble ethylenically unsaturated monomers are mixed with each other in advance, and mixed liquids thus obtained are mixed with each other, whereby polymerization is initiated. In addition, a multi-stage polymerization method in which the monomer is added multiple times may be used.

A temperature for the polymerization reaction varies depending upon a water-soluble radical polymerization initiator to be used, but from viewpoints that the reaction is smoothly performed by easily removing heat of polymerization while making the polymerization rapidly proceed and shortening the polymerization time to increase the economy, the temperature is preferably 20° C. to 110° C., and more preferably 40° C. to 90° C. The reaction time is usually 0.5 to 4 hours. Completion of the polymerization reaction can be confirmed by, for example, stopping a rise in the temperature within the reaction system. Thus, the water-absorbing resin particles are usually obtained in the state of a hydrous gel.

After the polymerization reaction, the obtained hydrous gel may be subjected to intermediate crosslinking By performing the intermediate crosslinking, the degree of crosslinking of the hydrous gel can be increased to improve the water absorption characteristics more preferably. The intermediate crosslinking can be carried out by adding a crosslinking agent to the hydrous gel after the polymerization reaction, followed by heating.

Examples of the crosslinking agent for performing the intermediate crosslinking include polyols such as ethylene glycol, propylene glycol, 1,4-butanediol, trimethylolpropane, glycerin, polyoxyethylene glycol, polyoxypropylene glycol, and polyglycerin; compounds having two or more epoxy groups, such as (poly)ethylene glycol diglycidyl ether, (poly)propylene glycol diglycidyl ether, and (poly)glycerin diglycidyl ether; haloepoxy compounds such as epichlorohydrin, epibromohydrin, and α-methyl epichlorohydrin; compounds having two or more isocyanate groups such as 2,4-tolylene diisocyanate and hexamethylene diisocyanate; oxazoline compounds such as 1,2-ethylenebisoxazoline; carbonate compounds such as ethylene carbonate; and hydroxyalkylamide compounds such as bis[N,N-di(β-hydroxyethyl)]adipamide. Among these, the polyglycidyl compounds such as (poly)ethylene glycol diglycidyl ether, (poly)glycerin diglycidyl ether, (poly)glycerin triglycidyl ether, (poly)propylene glycol polyglycidyl ether, and polyglycerol polyglycidyl ether are preferable. These crosslinking agents may be used alone or in combination of two or more kinds thereof.

From the viewpoints of suppressing the properties of water solubility by appropriately crosslinking the obtained hydrous gel and exhibiting favorable water absorption characteristics, the amount of the crosslinking agent used for the intermediate crosslinking is preferably 0 to 0.03 moles, more preferably 0 to 0.01 moles, and still more preferably 0 to 0.005 moles, per 1 mole of the water-soluble ethylenically unsaturated monomer.

Subsequently, in order to remove moisture from the obtained hydrous gel, drying is performed. Examples of the drying method include (a) method in which azeotropic distillation is performed by heating from the outside in the state where the hydrous gel is dispersed in a hydrocarbon dispersion medium, and the hydrocarbon dispersion medium is refluxed to remove moisture, (b) method in which a polymer in the form of a hydrous gel is taken out by decantation and dried under reduced pressure, and (c) method in which a polymer in the form of a hydrous gel is separated by filtration with a filter and dried under reduced pressure. Among these, (a) method is preferably used due to simplicity in a production process.

Control over the particle diameter of the water-absorbing resin particle can be performed by, for example, adjusting the rotational speed of a stirrer during the polymerization reaction or by adding a powdery inorganic flocculating agent to the system after the polymerization reaction or at an initial time of drying. The particle diameter of the obtained water-absorbing resin particle can be increased by the addition of the flocculating agent. Examples of the powdery inorganic flocculating agent include silica, zeolite, bentonite, aluminum oxide, talc, titanium dioxide, kaolin, clay, and hydrotalcite, and among these, from a viewpoint of the aggregation effect, silica, aluminum oxide, talc, or kaolin is preferable.

In the reverse-phase suspension polymerization, as a method of adding the powdery inorganic flocculating agent, a method in which a powdery inorganic flocculating agent is dispersed in the same kind of a hydrocarbon dispersion medium as that for use in the polymerization or water in advance, followed by performing mixing in a hydrocarbon dispersion medium containing a hydrous gel under stirring, is preferable.

The amount of the powdery inorganic flocculating agent to be added is preferably 0.001 to 1 part by mass, more preferably 0.005 to 0.5 parts by mass, and still more preferably 0.01 to 0.2 parts by mass, with respect to 100 parts by mass of the water-soluble ethylenically unsaturated monomers. By adjusting the amount of the powdery inorganic flocculating agent to be added to be within the range, it is easy to obtain water-absorbing resin particles having a desired particle size distribution.

The above-mentioned initial time in drying indicates, for example, a state where a water content of the hydrous gel is 50% by mass or more in a drying process after the polymerization reaction. As a specific time point for adding the powdery inorganic flocculating agent according to the present embodiment, a time point at which the water content of the hydrous gel is 50% by mass or more is preferable, a time point at which the water content of the hydrous gel is 55% by mass or more is more preferable, and a time point at which the water content of the hydrous gel is 60% by mass or more is still more preferable.

The water content of the hydrous gel is calculated by the following formula.

Water content=($Ww$)÷($Ww$+$Ws$)×100[% by mass]

$Ww$: The amount of moisture of a hydrous gel obtained by adding an amount of moisture used, as desired, upon mixing a powdery inorganic flocculating agent, a post-crosslinking agent, and the like to the amount obtained by subtracting the amount of moisture extracted to the outside by the drying process from the amount of moisture contained in the aqueous liquid before polymerization in an entire polymerization process.

$Ws$: A solid fraction amount calculated from the amount of materials such as water-soluble ethylenically unsaturated monomers, a crosslinking agent, and an initiator, each of which constitutes the hydrous gel polymer, to be introduced.

In the production of the water-absorbing resin particles according to the present embodiment, it is preferable that a surface portion of the hydrous gel is crosslinked (post-crosslinked) using a crosslinking agent in the drying process or any of the following processes. It is preferable that post-crosslinking is performed at the timing when the hydrous gel has a specific water content. The time of the post-crosslinking is preferably a time point at which the water content of the hydrous gel is 10% to 60% by mass, more preferably a time point at which the water content of the hydrous gel is 20% to 55% by mass, and still preferably a time point at which the water content of the hydrous gel is 30% to 50% by mass.

Examples of the post-crosslinking agent for performing post-crosslinking include compounds having two or more reactive functional groups. Examples of the post-crosslinking agent include polyols such as ethylene glycol, propylene glycol, 1,4-butanediol, trimethylolpropane, glycerin, polyoxyethylene glycol, polyoxypropylene glycol, and polyglycerin; polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, and (poly)glycerol polyglycidyl ether; haloepoxy compounds such as epichlorohydrin, epibromohydrin, and α-methyl epichlorohydrin; isocyanate compounds such as 2,4-tolylene diisocyanate and hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, and 3-butyl-3-oxetane ethanol; oxazoline compounds such as 1,2-ethylenebisoxazoline; carbonate compounds such as ethylene carbonate; and hydroxyalkylamide compounds such as bis[N,N-di(β-hydroxyethyl)]adipamide. Among these, the polyglycidyl compounds such as (poly)ethylene glycol diglycidyl ether, (poly)glycerin diglycidyl ether, (poly)glycerin triglycidyl ether, (poly)propylene glycol polyglycidyl ether, and polyglycerol polyglycidyl ether are more preferable. These post-crosslinking agents may be used alone or in combination of two or more kinds thereof.

The amount of the post-crosslinking agent cannot be absolutely determined since it varies depending on the type of the post-crosslinking agent, but the amount is usually a ratio of 0.00001 to 0.02 moles, preferably 0.0001 to 0.01 moles, and more preferably 0.0005 to 0.005 moles, in terms of a ratio with respect to 1 mole of the water-soluble ethylenically unsaturated monomers used for polymerization.

From a viewpoint of sufficiently increasing the crosslinking density in the surface portion of the water-absorbing resin particles to enhance the gel strength of the water-absorbing resin particles, the amount of the post-crosslinking agent to be used is preferably 0.00001 moles or more, and from a viewpoint of increasing the water retention capacity of the water-absorbing resin particles, the amount of the post-crosslinking agent to be used is preferably 0.02 moles or less.

In the production of the water-absorbing resin particles according to the present embodiment, a polyvalent metal compound may be used as a crosslinking agent, for example. The water-absorbing resin particles according to the embodiment may not contain the polyvalent metal compound.

A dried product of the surface-crosslinked water-absorbing resin particles can be obtained by distilling off water and the hydrocarbon dispersion medium by a known method after the post-crosslinking reaction. Water may be added to the particles during the drying. Water can be added, for example by spraying.

The water-absorbing resin particles according to the present embodiment can be used in mixture with, for example, a gel stabilizer, a metal chelating agent, silica, or the like. The water-absorbing resin particles according to the present embodiment can be made to have a desired particle size distribution at the time point obtained by the above-mentioned production method, but the particle size distribution may be set to a predetermined particle size distribution by further performing operations such as adjustment of a particle size through classification with a sieve.

In the water-absorbing resin particles according to the present embodiment, for example, a proportion of the particles having a particle diameter of more than 250 μm and 850 μm or less may be 70% by mass or more, 75% by mass or more, 80% by mass or more, 85% by mass or more, or 90% by mass or more, with respect to the total amount of the water-absorbing resin particles. In the water-absorbing resin particles according to the present embodiment, a proportion of the particles having a particle diameter of 250 μm or less may be 20% by mass or less, 18% by mass or less, 15% by mass or less, or 10% or less, with respect to the total amount of the water-absorbing resin particles.

The water-absorbing resin particles according to the present embodiment may have a median particle diameter of, for example, 250 to 850 μm, and the median particle diameter is preferably 300 to 700 μm, and more preferably 300 to 500 μm.

The water-absorbing resin particles generally take shapes such as a substantial spherical shape, a crushed shape, a granular shape, and aggregates thereof, depending on a production method thereof. From a viewpoint of more making it easier to obtain the effect of the invention of the present application, the water-absorbing resin particles according to the present embodiment may be, for example, in the granular shape. The granular shape in the present specification indicates that particles have a number of projections on surfaces thereof, and can also be mentioned as a fine uneven shape. The water-absorbing resin particles according to the present embodiment may also be aggregates of granular particles.

The water-absorbing resin particles according to the present embodiment can be suitably used in the field of sanitary goods such as paper diapers, incontinence pads, and sanitary napkins.

The water-absorbing resin particles according to the present embodiment can be suitably used for an absorbent. The absorbent may comprise, for example, an absorbent core including water-absorbing resin particles, and core wraps for retaining the absorbent core. The core wraps may be, for example, a tissue, a non-woven fabric, or the like. The core wraps may be disposed to hold the absorbent core therebetween, or may have a form of wrapping the entire absorbent core. The absorbent may be formed of only the absorbent core. The absorbent core may further comprise a fibrous material.

Examples of the fibrous material include cellulose-based fibers such as finely pulverized wood pulp, cotton, cotton linter, rayon, and cellulose acetate, and synthetic fibers such as polyamides, polyesters, and polyolefins. In addition, the fibrous materials may be a mixture of the above-mentioned fibers.

Fibers may adhere to each other by adding an adhesive binder to the fibrous material in order to enhance the shape retention properties before or during use of the absorbents. Examples of the adhesive binder include hot-melt synthetic fibers, hot-melt adhesives, and adhesive emulsions.

Examples of the hot-melt synthetic fibers include full-melt binders such as polyethylene, polypropylene, and an ethylene-propylene copolymer; and partial-melt hinders formed of polypropylene and polyethylene in a side-by-side or core-and-sheath configuration. In the above-mentioned partial-melt binders, the polyethylene portion alone is hot-melted. Examples of the hot-melt adhesive include a blend of a base polymer such as an ethylene-vinyl acetate copolymer, a styrene-isoprene-styrene block copolymer, a styrene-butadiene-styrene block copolymer, a styrene-ethylene-butylene-styrene block copolymer, a styrene-ethylene-propylene-styrene block copolymer, and an amorphous polypropylene with a tackifier, a plasticizer, an antioxidant, or the like.

Examples of the adhesive emulsions include polymers of at least one or more monomers selected from the group consisting of methyl methacrylate, styrene, acrylonitrile, 2-ethylhexyl acrylate, butyl acrylate, butadiene, ethylene, and vinyl acetate. These adhesive binders may be used alone or in combination of two or more kinds thereof.

The configuration of the absorbent core may be, for example, a form in which water-absorbing resin particles and the fibrous materials are uniformly mixed, a form in which water-absorbing resin particles are held between fibrous materials formed in the sheet shape or layer shape, or another form.

In the absorbent core, a proportion of the water-absorbing resin particles with respect to the total amount of the water-absorbing resin particles and the fibrous materials may be, for example, 2% by mass or more, 5% by mass or more, 10% by mass or more, 20% by mass or more, 30% by mass or more, 50% by mass or more, 70% by mass or more, 80% by mass or more, 90% by mass or more, 95% by mass or more, or 98% by mass or more. The proportion of the water-absorbing resin particles with respect to the total amount of the water-absorbing resin particles and the fibrous materials may be, for example, 100% by mass or less, 95% by mass or less, 90% by mass or less, 80% by mass or less, 70% by mass or less, 60% by mass or less, or 50% by mass or less. That is, the proportion of the water-absorbing resin particles with respect to the total amount of the water-absorbing resin particles and the fibrous materials may be, for example, 2% to 100% by mass, 50% to 100% by mass, 60% to 100% by mass, or 70% to 100% by mass.

Since the water-absorbing resin particles according to the present embodiment have an excellent elasticity after absorbing water (after swelling), the absorbent comprising the water-absorbing resin particles can have a sufficiently high elasticity even in a case where a proportion of the fibrous materials in the absorbent core in the absorbent is low in addition, since the absorbent comprising the water-absorbing resin particles can maintain a high elasticity even though a proportion of the fibrous materials in the absorbent core is low, the absorbent can be made thin without impairing the absorption performance.

An absorbent article according to the present embodiment comprises the above-mentioned water-absorbing resin particles. The absorbent article according to the present embodiment comprises, for example, a liquid-permeable sheet, the absorbent, and a liquid-impermeable sheet in this order. The absorbent article can be applied to sanitary goods such as paper diapers, incontinence pads, and sanitary napkins. Since the water-absorbing resin particles have an excellent elasticity after absorbing water, the absorbent article comprising the water-absorbing resin particles can have a highly flexible feeling, and can also have an excellent fit feeling when in use.

Examples of the material for the liquid-permeable sheet include non-woven fabrics formed of polyolefins such as polyethylene and polypropylene, polyesters, polyamides, or the like, and porous synthetic resin films. Examples of the material for the liquid-impermeable sheet include synthetic resin films formed of polyethylene, polypropylene, ethylene vinyl acetate, polyvinyl chloride, or the like; films formed of composites of these synthetic resins and non-woven fabrics; and films formed of composites of these synthetic resins with woven fabrics. These liquid-impermeable sheets may also be endowed with vapor-transmitting properties.

The absorbent and the absorbent article may further comprise components such as amorphous silica, deodorants, antibacterial agents, and fragrances.

EXAMPLES

Hereinafter, the present invention will be described in more detail with reference to Examples, but the present invention is not limited to these Examples.

Example 1

A cylindrical round-bottomed separable flask including side wall baffles at four locations (baffle width: 7 mm) with an inner diameter of 110 mm and a capacity of 2 L, which was equipped with a reflux condenser, a dropping funnel, a nitrogen gas introduction tube, and a stirrer, was prepared. As the stirrer, stirring blades having four inclined paddle blades (surface-treated with a fluororesin) with a blade diameter of 50 min in two stages were used. 660 ml of n-heptane as a petroleum-based hydrocarbon dispersion medium was put into the flask, 0.984 g of sorbitan monolaurate as a surfactant (Nonion LP-20R, HLB value of 8.6, manufactured by NOF Corporation) was added thereto, and the mixture was heated to 50° C. at a rotational speed of the stirrer of 300 rpm. Sorbitan monolaurate was dissolved in n-heptane by heating, and then an internal temperature was lowered to 40° C.

92 g (1.02 moles) of an 80% by mass aqueous acrylic acid solution was put into an Erlenmeyer flask having a capacity of 500 ml, and 146 g of a 21% by mass aqueous sodium hydroxide solution was added dropwise thereto under ice-cooling of the aqueous acrylic acid solution from the outside to perform neutralization of acrylic acid. Next, 0.101 g (0.374 mmol) of potassium persulfate as a radical polymerization initiator was added to a partially neutralized aqueous acrylic acid solution thus obtained and dissolved to prepare an aqueous monomer solution.

The aqueous monomer solution was added to the separable flask and the inside of the system was sufficiently replaced with nitrogen. Then, a rotational speed of the stirrer was set to 700 rpm, and the flask was immersed in a water bath at 70° C. and maintained for 60 minutes.

A liquid was prepared by dispersing 0.092 g of amorphous silica (Camlex #80, manufactured by Evonik Degussa Japan, Inc.) as a powdery inorganic flocculating agent in 100 g of n-heptane. In the separable flask, a rotational speed of the stirrer was set to 1,000 rpm, and the above liquid was added to a polymerization solution containing the produced hydrous gel, n-heptane, and a surfactant, and mixed for 10 minutes. Then, the flask containing a reaction solution was immersed in an oil bath at 125° C., and 109 g of water was extracted out of the system while n-heptane was refluxed by azeotropic distillation with n-heptane and water. Then, 9.94 g (2.85 mmol) of a 5% by mass aqueous ethylene glycol diglycidyl ether solution as a post-crosslinking agent was added to the flask, and the mixture was maintained at an internal temperature of 80± 2° C. for 2 hours.

After that, water and n-heptane were evaporated and the residue was dried until almost no evaporation substance from the inside of the system was distilled off, then the flask was once removed from the oil bath and 13.8 g of water was sprayed with a spray at a flow rate of 0.3 g per second. Then, the state was maintained at 80° C. for 30 minutes while nitrogen is blown into the system at a flow rate of 200 ml per minute to obtain a dried product. The dried product was passed through a sieve having a mesh size of 850 µm to obtain 90.5 g of water-absorbing resin particles. The obtained water-absorbing resin particles were in the form in which granular (fine uneven) particles were aggregated.

In the obtained water-absorbing resin particles, a proportion of the particles having a size of more than 250 µm and 850 µm or less was 96% by mass and a proportion of the particles having a size of 250 µm or less was 4% by mass, with respect to all the particles. A median particle diameter was 410 µm.

Example 2

90.4 g of water-absorbing resin particles were obtained in the same manner as in Example 1 except that the amount of water extracted out of the system by azeotropic distillation was changed to 117 g. The obtained water-absorbing resin particles were in the form in which granular (fine uneven) particles were aggregated. In the obtained water-absorbing resin particles, a proportion of the particles having a size of more than 250 µm and 850 µm or less was 94% by mass and a proportion of the particles having a size of 250 µm or less was 6% by mass, with respect to all the particles. A median particle diameter was 390 µm.

Example 3

90.5 g of water-absorbing resin particles were obtained in the same manner as in Example 1 except that the amount of water extracted out of the system by azeotropic distillation was changed to 112 g and 4.97 g (2.85 mmol) of a 10% by mass aqueous ethylene glycol diglycidyl ether solution was added instead of a 5% by mass aqueous ethylene glycol diglycidyl ether solution as a post-crosslinking agent. The obtained water-absorbing resin particles were in the form in which granular (fine uneven) particles were aggregated. In the obtained water-absorbing resin particles, a proportion of the particles having a size of more than 250 µm and 850 µm or less was 91% by mass and a proportion of the particles having a size of 250 µm or less was 9% by mass, with respect to all the particles. A median particle diameter was 360 µm.

Example 4

90.4 g of water-absorbing resin particles were obtained in the same manner as in Example 3 except that the amount of water extracted out of the system by azeotropic distillation was changed to 108 g. The obtained water-absorbing resin particles were in the form in which granular (fine uneven) particles were aggregated. In the obtained water-absorbing resin particles, a proportion of the particles having a size of more than 250 µm and 850 µm or less was 91% by mass and a proportion of the particles having a size of 250 µm or less was 9% by mass, with respect to all the particles. A median particle diameter was 360 µm.

Comparative Example 1

A cylindrical round-bottomed separable flask including sidewall baffles at four locations (baffle width: 7 mm) with an inner diameter of 110 mm and a capacity of 2 L, which was equipped with a reflux condenser, a dropping funnel, a nitrogen gas introduction tube, and a stirrer, was prepared. As the stirrer, stirring blades having four inclined paddle blades (surface-treated with a fluororesin) with a blade diameter of 50 mm in two stages were used. 660 ml of n-heptane as a petroleum-based hydrocarbon dispersion medium was put into the flask, 1.10 g of sorbitan monolaurate as a surfactant (Nonion LP-20R, HLB due of 8.6, manufactured by NOF Corporation) was added thereto, and the mixture was heated to 50° C. at a rotational speed of the stirrer of 300 rpm. Sorbitan monolaurate was dissolved in n-heptane by heating, and then an internal temperature was lowered to 40° C.

On the other hand, 92 g (1.02 moles) of an 80% by mass aqueous acrylic acid solution was put into an Erlenmeyer flask having a capacity of 500 ml, and 146.0 g of a 21% by mass aqueous sodium hydroxide solution was added dropwise thereto under ice-cooling of the aqueous acrylic acid solution from the outside to perform neutralization of acrylic acid. Next, 0.101 g (0.374 mmol) of potassium persulfate as a radical polymerization initiator was added to a partially neutralized aqueous acrylic acid solution thus obtained and dissolved to prepare an aqueous monomer solution.

The aqueous monomer solution was added to the separable flask and the inside of the system was sufficiently replaced with nitrogen. Then, a rotational speed of the stirrer was set to 700 rpm, and the flask was immersed in a water bath at 70° C. and maintained for 60 minutes. 0.41 g (0.047 mmol) of a 2% by mass aqueous ethylene glycol diglycidyl ether solution as an intermediate-crosslinking agent was added to the flask and the mixture was maintained at 75° C. for 30 minutes.

A liquid prepared by dispersing 0.092 g of amorphous silica (Carplex #80, manufactured by Evonik Degussa Japan, Inc.) as a powdery inorganic flocculating agent in 100 g of n-heptane was prepared. In the separable flask, a rotational speed of the stirrer was set to 1,000 rpm, and the above liquid was added to a polymerization solution containing a hydrous gel, n-heptane, and a surfactant, and mixed for 10 minutes. Then, a reaction solution in the flask was heated in an oil bath at 125° C., and 129 g of water was extracted out of the system while n-heptane was refluxed by azeotropic distillation with n-heptane and water. Then, 4.14 g (0.48 mmol) of a 2% by mass aqueous ethylene glycol diglycidyl ether solution as a post-crosslinking agent was added to the flask, and the mixture was maintained at 80° C. for 2 hours.

After that, water and n-heptane were evaporated and the residue was dried while nitrogen is blown into the system at a flow rate of 200 ml per minute to obtain a dried product. The dried product was passed through a sieve having a mesh size of 850 μm to obtain 90.0 g of water-absorbing resin particles. The obtained water-absorbing resin particles were in the form in which granular (fine uneven) particles were aggregated.

In the obtained water-absorbing resin particles, a proportion of the particles having a size of more than 250 μm and 850 μm or less was 92% by mass and a proportion of the particles having a size of 250 μm or less was 8% by mass, with respect to all the particles. A median particle diameter was 350 μm.

Comparative Example 2

A cylindrical round-bottomed separable flask with an inner diameter of 110 mm and a capacity of 2 L, which was equipped with a reflux condenser, a dropping funnel, a nitrogen gas introduction tube, and a stirrer, was prepared. As the stirrer, stirring blades having four inclined paddle blades with a blade diameter of 50 mm in two stages were used. 300 g of n-heptane as a petroleum-based hydrocarbon dispersion medium was put into the flask, and 0.74 g of sucrose stearic acid ester (RYOTO sugar ester 5-370, HLB value of 3, manufactured by Mitsubishi-Chemical Foods Corporation) as a surfactant and 0.74 g of a maleic anhydride-modified ethylene-propylene copolymer (HI-WAX 1105A, manufactured by Mitsui Chemicals, Inc.) as a polymer dispersant were added thereto, and the mixture was heated to 80° C. at a rotational speed of the stirrer of 300 rpm. The surfactant was dissolved by heating and then cooled to 50° C.

92 g (1.02 moles) of an 80% by mass aqueous acrylic acid solution was put into an Erlenmeyer flask having a capacity of 500 mL, and 102.2 g of a 30% by mass aqueous sodium hydroxide solution was added dropwise thereto under cooling of the aqueous acrylic acid solution from the outside to perform neutralization of acrylic acid. After the neutralization, 0.092 g of hydroxyethyl cellulose (HEC AW-15F, manufactured by Sumitomo Seika Chemicals, Ltd.) as a thickener, 0.074 g (0.274 mmol) of potassium persulfate as a peroxide, 0.018 g (0.106 mmol) of ethylene glycol diglycidyl ether as an internal crosslinking agent, and 43.8 g of ion exchange water were added and dissolved to prepare an aqueous monomer solution.

The aqueous monomer solution was added to the separable flask and the inside of the system was sufficiently replaced with nitrogen. Then, a rotational speed of the stirrer was set to 500 rpm, and the flask was immersed in a water bath at 70° C. and maintained for 60 minutes to obtain a first-stage polymerized slurry.

128.8 g (1.43 moles) of an 80% by mass aqueous acrylic acid solution was put into another Erlenmeyer flask having a capacity of 500 and 143.1 g of a 30% by mass aqueous sodium hydroxide solution was added dropwise thereto under cooling of the aqueous acrylic acid solution from the outside to perform neutralization of acrylic acid. After the neutralization, 0.104 g (0.382 mmol) of potassium persulfate as a peroxide, 0.039 g (0.222 mmol) of ethylene glycol diglycidyl ether as an internal crosslinking agent, and 15.9 g of ion exchange water were added to the flask and dissolved to prepare a second-stage aqueous monomer solution.

After that, a rotational speed of the stirrer was set to 1,000 rpm, the inside of the separable flask system was cooled to 25° C., and then the total amount of the second-stage aqueous monomer solution was added to the first-stage polymerized slurry. After the addition, the inside of the system was sufficiently replaced with nitrogen, and the flask was again immersed in a water bath at 70° C. and maintained for 30 minutes.

After that, a reaction solution in the flask was heated in an oil bath at 125° C., and 273 g of water was extracted out of the system while n-heptane was refluxed by azeotropic distillation with n-heptane and water. Then, 6.63 g (0.761 mmol) of a 2% by mass aqueous ethylene glycol diglycidyl ether solution as a post-crosslinking agent was added to the flask, and the mixture was maintained at 80° C. for 2 hours. After that, water and n-heptane were evaporated and the residue was dried while nitrogen is blown into the system at a flow rate of 200 ml per minute to obtain a dried product. This dried product was passed through a sieve having a mesh size of 850 μm to obtain 231.2 g of water-absorbing resin particles in the form in which spherical particles were aggregated.

In the obtained water-absorbing resin particles, a mass proportion of the particles having a size of 150 to 850 μm was 94% by mass with respect to the total proportion, and a median particle diameter was 390 μm.

Comparative Example 3

A cylindrical round-bottomed separable flask with an inner diameter of 110 mm and a capacity of 2 L, which was equipped with a reflux condenser, a dropping funnel, a nitrogen gas introduction tube, and a stirrer, was prepared. As the stirrer, stirring blades having four inclined paddle blades with a blade diameter of 50 mm in two stages were used. 300 g of n-heptane as a petroleum-based hydrocarbon dispersion medium was put into the flask, and 0.74 g of sucrose stearic acid ester (RYOTO sugar ester S-370, HLB value of 3, manufactured by Mitsubishi-Chemical Foods Corporation) as a surfactant and 0.74 g of a maleic anhydride-modified ethylene-propylene copolymer (HI-WAX 1105A, manufactured by Mitsui Chemicals, Inc.) as a polymer dispersant were added thereto, and the mixture was heated to 80° C. at a rotational speed of the stirrer of 300 rpm. The surfactant was dissolved by heating and then cooled to 50° C.

92 g (1.02 moles) of an 80% by mass aqueous acrylic acid solution was put into an Erlenmeyer flask having a capacity of 500 mL, and 146.0 g of a 21% by mass aqueous sodium hydroxide solution was added dropwise thereto under cooling of the aqueous acrylic acid solution from the outside to perform neutralization of acrylic acid. After the neutralization, 0.092 g of hydroxylethyl cellulose (HEC AW-15F, manufactured by Sumitomo Seika Chemicals, Ltd.) as a thickener, 0.074 g (0.274 mmol) of potassium persulfate as a peroxide, and 0.0156 g (0.0895 mmol) of ethylene glycol diglycidyl ether as an internal crosslinking agent were added and dissolved to prepare an aqueous monomer solution.

The aqueous monomer solution was added to the separable flask and the inside of the system was sufficiently replaced with nitrogen. Then, a rotational speed of the stirrer was set to 500 rpm, and the flask was immersed in a water bath at 70° C. and maintained for 60 minutes to obtain a first-stage polymerized slurry.

128.8 g (1.43 moles) of an 80% by mass aqueous acrylic acid solution was put into another Erlenmeyer flask having a capacity of 500 mL, and 159.0 g of a 27% by mass aqueous sodium hydroxide solution was added dropwise thereto under cooling of the aqueous acrylic acid solution from the outside to perform neutralization of acrylic acid. After the neutralization, 0.104 g (0.382 mmol) of potassium persulfate as a peroxide and 0.0155 g (0.0890 mmol) of ethylene glycol diglycidyl ether as an internal crosslinking agent were added thereto and dissolved to prepare a second-stage aqueous monomer solution.

After that, a rotational speed of the stirrer was set to 1,000 rpm, the inside of the separable flask system was cooled to 25° C., and the total amount of the second-stage aqueous monomer solution was added to the first-stage polymerized slurry. After the addition, the inside of the system was sufficiently replaced with nitrogen, and the flask was again immersed in a water bath at 70° C. and maintained for 30 minutes.

After that, a reaction solution in the flask was heated in an oil bath at 125° C., and 273 g of water was extracted out of the system while n-heptane was refluxed by azeotropic distillation with n-heptane and water. Then, 6.62 g (0.76 mmol) of a 2% by mass aqueous ethylene glycol diglycidyl ether solution as a post-crosslinking agent was added to the flask, and the mixture was maintained at 80° C. for 2 hours. Thereafter, n-heptane was evaporated and the residue was dried to obtain a dried product. 0.3% by mass of amorphous silica (Carplex #80, manufactured by Evonik Degussa Japan, Inc.) was mixed with the dried product. The obtained mixture was passed through a sieve having a mesh size of 850 μm to obtain 231.4 g of water-absorbing resin particles in the form in which spherical particles were aggregated.

In the obtained water-absorbing resin particles, a mass proportion of the particles having a size of 150 to 850 μm was 97.1% by mass with respect to the total proportion, and a median particle diameter was 360 μm.

Comparative Example 4

195.36 g of 100% acrylic acid was added to a separable flask having a capacity of 2 L. 135.13 g of ion exchange water was added while stirring the inside of the separable flask, and 357.93 g of 30% sodium hydroxide was added dropwise under an ice bath. Then, 104.73 g of 100% acrylic acid was added to prepare a partially neutralized acrylic acid solution having a degree of neutralization of 65 mol %.

780 g of the partially neutralized acrylic acid solution having a degree of neutralization of 65 mol %, 43.78 g of a 2% polyethylene glycol diacrylate (average repeating unit of ethylene oxide: 9) aqueous solution as an internal crosslinking agent solution, and 180.7 g of ion exchange water were introduced into a plastic bottle having a capacity of 2 L and mixed to prepare an aqueous monomer solution. The dissolved oxygen in the solution was adjusted to 0.1 ppm or less by pouring the aqueous monomer solution into a stainless steel vat and blowing nitrogen into the vat. Subsequently, under a nitrogen atmosphere, the temperature of the aqueous monomer solution was adjusted to 18° C., and then, under stirring, 1.58 g of a 5% aqueous sodium persulfate solution, 1.58 g of a 5% 2,2'-azobis(2-amidinopropane) dihydrochloride aqueous solution, 1.50 g of a 0.5% L-ascorbic acid aqueous solution, and 1.70 g of a 0.35% hydrogen peroxide aqueous solution were added dropwise in this order. After the hydrogen peroxide aqueous solution was added dropwise, the stirring was stopped. Polymerization was initiated immediately after the stop of the stirring, and after 9 minutes, the temperature of the aqueous monomer solution reached a peak temperature of 86° C. Subsequently, the vat was immersed in a hot water bath at 80° C. and maintained for 10 minutes to obtain a hydrous gel of a crosslinked polymer.

Subsequently, the obtained hydrous gel of the crosslinked polymer was cooled to 30° C. The water content of the hydrous gel of the crosslinked polymer after the cooling was 63%. The hydrous gel of the crosslinked polymer was roughly crushed with a double-arm kneader having a capacity of 1 L and then dried at 180° C. for 30 minutes to obtain a dried product. After that, the dried product was crushed using a crusher (rotor beater mill) with a screen hole size of 1 mm After the crushing, a crushed material of 850 μm or more and a crushed material of less than 150 μm were removed to obtain water-absorbing resin particles having a median particle diameter of 380 μm (a mass proportion of the particles having a size of 150 μm or more and less than 850 μm was 100% by mass with respect to the total proportion).

[Evaluation Test of Water-Absorbing Resin Particles]

The water-absorbing resin particles obtained in Examples and Comparative Examples described above were subjected to various tests shown below and evaluated. The results are shown in Table 1.

(1) Retention Capacity of Physiological Saline

A cotton bag (cotton broadcloth No. 60, 100 mm in width×200 mm in length) in which 2.00 g of the water-absorbing resin particles had been weighed was placed in a beaker having a capacity of 500 mL. 500 g of a 0.9% by mass sodium chloride aqueous solution (physiological saline) was poured into the cotton bag having the water-absorbing resin particles therein at once so that a lump could not be formed, and the upper part of the cotton bag was closed with a rubber band and left to stand for 30 minutes so that the water-absorbing resin particles were swollen. The cotton bag after an elapse of 30 minutes was dehydrated for 1 minute using a dehydrator (manufactured by Kokusan Co., Ltd., product number: H-122) which had been set at a centrifugal force of 167 G, and the mass Wa (g) of the cotton bag containing the swollen gel after dehydration was measured. By performing the same operation without addition of the water-absorbing resin particles, the mass Wb (g) of the empty cotton bag upon wetting was measured, and a retention capacity of physiological saline was calculated by the following formula:

Retention capacity of physiological saline (g/g)= [$Wa-Wb$]/2.00

(2) Absorption Rate of Physiological Saline

An absorption rate of physiological saline was measured by a vortex method in a room adjusted to 25° C.± 1° C. Specifically, 50± 0.1 g of physiological saline that had been put into a beaker having a capacity of 100 ml was adjusted to a temperature of 25° C.± 0.2° C. in a thermostatic water bath and then stirred at 600 rpm with a magnetic stirrer bar (8 mmφ×30 mm, no ring included) to generate a vortex. 2.0± 0.002 g of the water-absorbing resin particles were added into the physiological saline at once, and a time (sec) until the vortex disappeared and the liquid surface became flat after the addition of the water-absorbing resin particles was measured and the result was taken as an absorption rate of physiological saline of the water-absorbing resin particles:

(3) Particle Size Distribution 50 g of the water-absorbing resin particles were used for particle size distribution measurement. JIS standard sieves were combined in the following order from the top: a sieve with a mesh size of 850 μm, a sieve with a mesh size of 500 μm, a sieve with a mesh size of 425 μm, a sieve with a mesh size of 300 μm, a sieve with a mesh size of 250 μm, a sieve with a mesh size of 180 μm, a sieve with a mesh size of 150 μm, and a receiving tray.

The water-absorbing resin particles were fed to the topmost sieve in the combination and shaken for 20 minutes using a Ro-Tap shaker to conduct classification. After the classification, the mass of the water-absorbing resin particles remaining on each sieve was calculated as a mass percentage with respect to the total amount to determine a particle size distribution. By integrating the values on the sieves in descending order of the particle diameters with regard to the particle size distribution, the relationship between the mesh size of the sieve and the integrated value of the mass percentage of the water-absorbing resin particles remaining on the sieve was plotted on a logarithmic probability paper. By connecting the plotted points on the probability paper with straight lines, the particle diameter corresponding to 50% by mass of the integrated mass percentage was taken as a median particle diameter.

A presence proportion of the water-absorbing resin particles having a particle diameter of more than 250 μm and 850 μm or less is a sum of the proportions of the water-absorbing resin particles remaining on the sieves having mesh sizes of 500 μm, 425 μm, 300 μm, and 250 μm, and similarly, a presence proportion of the water-absorbing resin particles having a particle diameter of 250 μm or less is a numerical value obtained by adding up all the proportions of the water-absorbing resin particles remaining on the receiving tray and the sieves having mesh sizes of 180 μm and 150 μm.

(4) Repulsion Rate Test of Water-Absorbing Resin Particles

The FIGURE is a schematic view illustrating a method of measuring the repulsion rate of the water-absorbing resin particles according to the present embodiment. 6.0 g of ion exchange water 3 was put into a Petri dish 1 (device 1: inner diameter of 48 mm, height of 15 mm). Next, 0.20 g of water-absorbing resin particles 15 were uniformly sprinkled inside a device 2 formed of an acrylic cylinder 10 (inner diameter of 25.4 mm, height of 35.6 mm, mass of 17.1 g) having a bottom surface to which a 100 mesh wire mesh 11 is adhered and graduated at intervals of 1 mm in a vertical height direction, and an acrylic piston 17 (device 3: inner diameter of 25.2 mm, mass of 5.6 g) was placed on the upper part of the cylinder. The inside of a side wall 13 of the cylinder 10 can be visually checked. At the same time when the device 2 was placed on the device 1, a stopwatch was started (t=0 minutes) to cause the water-absorbing resin particles 15 to absorb water (The FIGURE at (a)). That is, the water-absorbing resin particles 15 are swollen by 30 times their own weight by the ion exchange water 3.

After 1 minute (t=1 minute), the free swelling height $h_1$ mm (height from the bottom surface of the device 2 to the bottom surface of the device 3 (height from the top surface of the wire mesh 11 to the bottom surface of the piston 17. The same applies hereinbelow.)) was read (The FIGURE at (b)). At the same time as reading the free swelling height $h_1$, a metal weight 19 (device 4: outer diameter of 19.1 mm, mass of 59.8 g) was placed on the device 3. In this case, the pressure applied to the water-absorbing resin particles 15 is $1.3 \times 10^3$ Pa (0.19 Psi) when the weight 19 and the piston 17 are combined. After further 1 minute (t=2 minutes), the height under load $h_2$ mm (height from the bottom surface of the device 2 to the bottom surface of the device 3) was read (The FIGURE at (c)). At the same time as reading the height under load $h_2$, the device 4 was removed and the load was released. After further 1 minute (t=3 minutes), the restored height $h_3$ mm after the load release (height from the bottom surface of the device 2 to the bottom surface of the device 3) was read (The FIGURE at (d)). Using the obtained numerical values of $h_1$ mm, $h_2$ mm, and $h_3$ mm, the repulsion rate was calculated from the following formula.

Repulsion rate (%)=$(h_3-h_2)/h_1 \times 100$

The water-absorbing resin particles of Examples 1 to 4 absorbed all the ion exchange water in the Petri dish within 1 minute from initiation of the water absorption.

TABLE 1

|  | Absorption rate of physiological saline (sec) | Retention capacity of physiological saline (g/g) | Free swelling height $h_1$ (mm) | Height under load $h_2$ (mm) | Restored height $h_3$ (mm) | Repulsion rate $(h_3 - h_2)/h_1 \times 100$ (%) | $h_2/h_1$ | $h_3/h_2$ |
|---|---|---|---|---|---|---|---|---|
| Example 1 | 4 | 19 | 23.5 | 19.2 | 22.9 | 15.7 | 0.82 | 1.19 |
| Example 2 | 4 | 28 | 17.6 | 14.4 | 16.3 | 10.8 | 0.82 | 1.13 |

TABLE 1-continued

|  | Absorption rate of physiological saline (sec) | Retention capacity of physiological saline (g/g) | Free swelling height $h_1$ (mm) | Height under load $h_2$ (mm) | Restored height $h_3$ (mm) | Repulsion rate $(h_3 - h_2)/h_1 \times 100$ (%) | $h_2/h_1$ | $h_3/h_2$ |
|---|---|---|---|---|---|---|---|---|
| Example 3 | 5 | 36 | 14.3 | 12.7 | 13.6 | 6.3 | 0.89 | 1.07 |
| Example 4 | 4 | 31 | 14.3 | 11.5 | 12.9 | 9.7 | 0.80 | 1.13 |
| Comparative Example 1 | 4 | 34 | 11.9 | 11.6 | 11.6 | 0.3 | 0.97 | 1.00 |
| Comparative Example 2 | 43 | 31 | 15.0 | 14.4 | 15.0 | 3.9 | 0.96 | 1.04 |
| Comparative Example 3 | 37 | 43 | 12.2 | 12.1 | 12.5 | 3.1 | 0.99 | 1.03 |
| Comparative Example 4 | 70 | 40 | 12.0 | 12.3 | 12.6 | 2.3 | 1.03 | 1.02 |

[Evaluation of Absorbent Article]

(1) Preparation of Absorbent and Absorbent Article

Absorbents and absorbent articles were prepared using the water-absorbing resin particles obtained in Examples and Comparative Examples. 0.52 g of water-absorbing resin particles were uniformly sprinkled onto a spunbond-meltblown-meltblown-spunbond (SMMS) non-woven fabric (16 cm×5 cm) having a basis weight of 12 g/m² and then held with an SMMS non-woven fabric of the same size from above. Thus, a sheet-shaped absorbent was prepared. Further, an air-through type porous liquid-permeable sheet made of polyethylene-polypropylene, which has the same size as the absorbent and has a basis weight of 22 g/m², was disposed on the upper surface of the absorbent, and a liquid-impermeable sheet made of polyethylene, which has the same size and the same basis weight, was disposed on the lower surface of the absorbent to make the absorbent held therebetween. Thus, an absorbent article having a basis weight of water-absorbing resin particles of 65 g/m² was obtained.

(3) Elasticity Evaluation Test (Sensory Test) of Absorbent Article

The absorbent article was placed on a horizontal laboratory table. A 100 mL-dropping funnel with an opening of a liquid inlet adjusted to a flow rate of 8 mL/sec was installed so that the liquid inlet was positioned 1.5 cm above the center of the absorbent article, and then 15 mL of ion exchange water was introduced once from the top of the dropping funnel. One minute after the introduction, the dropping funnel was removed, and the panelist lightly pressed the upper surface of the absorbent article with his or her finger several times, and the elasticity (feeling of being pushed back) felt at that time was evaluated according to the following criteria. The test was conducted by five panelists (A to E), and the average value was defined as the elasticity of the absorbent article. The results are shown in Table 2.

<Evaluation Criteria for Elasticity>

5 points: Elasticity is extremely high.
4 points: Elasticity is relatively high.
3 points: Elasticity is at an acceptable level.
2 points: Elasticity is poor.
1 point: No elasticity is recognized.

TABLE 2

Evaluation test of elasticity of absorbent article (point)

|  | A | B | C | D | E | Average |
|---|---|---|---|---|---|---|
| Example 1 | 5 | 5 | 5 | 5 | 5 | 5.0 |
| Example 2 | 4 | 3 | 4 | 4 | 3 | 3.6 |
| Example 3 | 3 | 3 | 4 | 4 | 4 | 3.6 |
| Example 4 | 3 | 3 | 3 | 3 | 3 | 3.0 |
| Comparative Example 1 | 1 | 2 | 2 | 2 | 2 | 1.8 |
| Comparative Example 2 | 2 | 3 | 2 | 2 | 2 | 2.2 |
| Comparative Example 3 | 2 | 2 | 1 | 1 | 2 | 1.6 |
| Comparative Example 4 | 2 | 2 | 2 | 2 | 3 | 2.2 |

REFERENCE SIGNS LIST

1 ... Petri dish, 3 ... ion exchange water, 10 ... cylinder, 11 ... wire mesh, 13 ... side wall, 15 ... water-absorbing resin particles, 17 ... piston, 19 ... weight.

The invention claimed is:

1. Water-absorbing resin particles having a repulsion rate of 5% or more represented by Formula (1):

$$(h_3-h_2)/h_1 \times 100 (\%) \qquad (1)$$

wherein in Formula (1), when a cylinder with an inner diameter of 25.4 mm, which has a mesh-like bottom onto which 0.2 g of the water-absorbing resin particles are sprinkled, is placed in a container having ion exchange water in an amount of 30 times a mass of the water-absorbing resin particles such that the water-absorbing resin particles absorb the ion exchange water, $h_1$ represents a free swelling height (mm) of the water-absorbing resin particles after 1 minute from initiation of the water absorption, $h_2$ represents a height (mm) of the water-absorbing resin particles after a load of $1.3 \times 10^3$ Pa is applied to the water-absorbing resin particles for 1 minute after 1 minute from initiation of the water absorption, and $h_3$ represents a height (mm) of the water-absorbing resin particles after 1 minute from release of the load applied when measuring $h_2$.

2. The water-absorbing resin particles according to claim 1, wherein an absorption rate of physiological saline by a vortex method is 10 seconds or less.

3. The water-absorbing resin particles according to claim 1, wherein a retention capacity of physiological saline is 15 to 39 g/g.

4. The water-absorbing resin particles according to claim 1, wherein an absorption rate of physiological saline by a vortex method is 7 seconds or less.

* * * * *